United States Patent
Avery et al.

(10) Patent No.: US 6,830,897 B2
(45) Date of Patent: Dec. 14, 2004

(54) HIGH THROUGHPUT SCREEN FOR REDUCING DRUG CANDIDATE ATTRITION

(75) Inventors: Michael J. Avery, East Lyme, CT (US); Weichao G. Chen, Old Saybrook, CT (US); Hassan G. Fouda, Mystic, CT (US)

(73) Assignee: Pfizer Inc., New York, NY (US)

(*) Notice: Subject to any disclaimer, the term of this patent is extended or adjusted under 35 U.S.C. 154(b) by 20 days.

(21) Appl. No.: 09/837,674

(22) Filed: Apr. 18, 2001

(65) Prior Publication Data

US 2002/0034729 A1 Mar. 21, 2002

Related U.S. Application Data

(60) Provisional application No. 60/199,698, filed on Apr. 26, 2000.

(51) Int. Cl.[7] ............................ C12Q 1/48; C12Q 1/00; G01N 33/535
(52) U.S. Cl. ............................ 435/15; 435/4; 435/964
(58) Field of Search ............................ 435/15, 4, 964

(56) References Cited

U.S. PATENT DOCUMENTS

| | | | | |
|---|---|---|---|---|
| 5,478,723 A | * | 12/1995 | Parkinson et al. | 435/4 |
| 5,891,696 A | * | 4/1999 | Shaw et al. | 435/189 |
| 6,004,927 A | * | 12/1999 | Benet et al. | 514/9 |

FOREIGN PATENT DOCUMENTS

| | | | |
|---|---|---|---|
| JP | 10-207105 | 8/1998 | C12Q/1/26 |

OTHER PUBLICATIONS

Nikolic, D., et al. "Screening for Xenobiotic Electrophilic Metabolites Using Pulsed Ultrafiltration–Mass Spectrometry", (1999), vol. 2, No. 3, pp. 165–175.

D. Nikolic et al., Combinatorial Chemistry & High Throughput Screening, 1999, vol. 2, pp. 165–175, "Screening for Xenobiotic Electrophilic Metabolites Using Pulsed Ultrafiltration–Mass Spectrometry".

R.B. Van Breeman et al., Drug Metabolism and Disposition, 1998, vol. 26, No. 2, pp. 85–90, "Metabolic Screening Using On–line Ultrafiltration Mass Spectrometry".

JP–10–207105 Equivalent –U.S. Appl. No. 5,989,844, Date of Patent–Nov. 23, 1999, Shimada et al.

Japanese Article –The Practice of Medicinal Chemistry, Edited by Camille G. Wermuth, 1998, pp. 98–103, Published by Technomic.

English Equivalent Article –The Practice of Medicinal Chemistry, Edited by Camille G. Wermuth, 1996, pp. 82–99, Published by Academic Press.

Nelson, S. D. (1982) Metabolic activation and drug toxicity. *J. Med. Chem.* 25, 753–65.

Pirmohamed, M., Madden, S., & Park, B. K. (1996) Idiosyncratic drug reactions. *Clin. Pharmacokinet.* 31, 215–230.

Prescott, L. F. (1983) Reactive metabolites as a cause of hepatotoxicity. Int. *J. Clin. Pharm.* 3, 437–441.

Guengerich, F. P. (1992) Metabolic activation of carcinogens. *Pharmacol. Ther.* 54, 17–61.

Juchau, M. R., Lee, Q. P., & Fantel, A. G. (1992) Xenobiotic biotransformation/ bioactivation in organogenesis–stage conceptal issues: implications for embryotoxicity and teratogenesis. *Drug Metabolishm Reviews* 24(2), 195–238.

(List continued on next page.)

*Primary Examiner*—Louise N. Leary
(74) *Attorney, Agent, or Firm*—Peter C. Richardson; Gregg C. Benson; Kathleen A. Ranney

(57) ABSTRACT

This invention provides a high throughput method for identifying drug candidates which produce reactive metabolites that contribute to toxicity of the drug product.

8 Claims, 13 Drawing Sheets

OTHER PUBLICATIONS

Figure 1A:
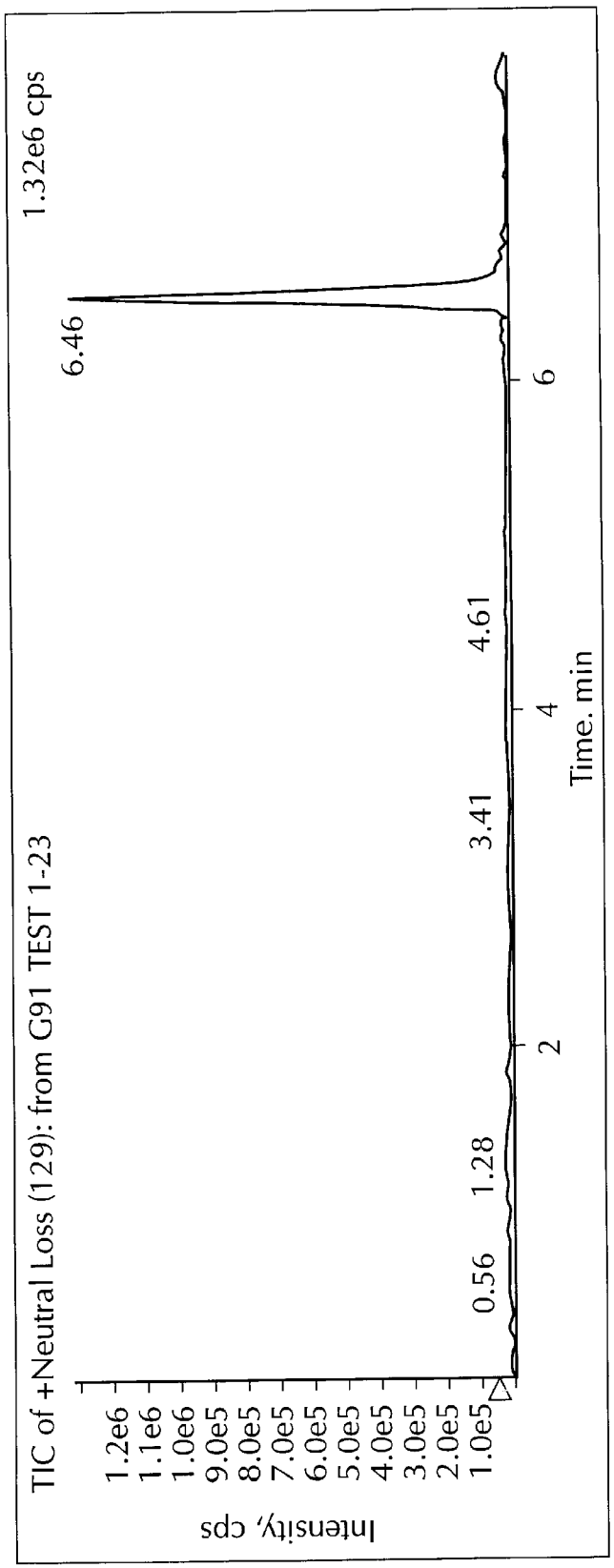
Figure 1D:
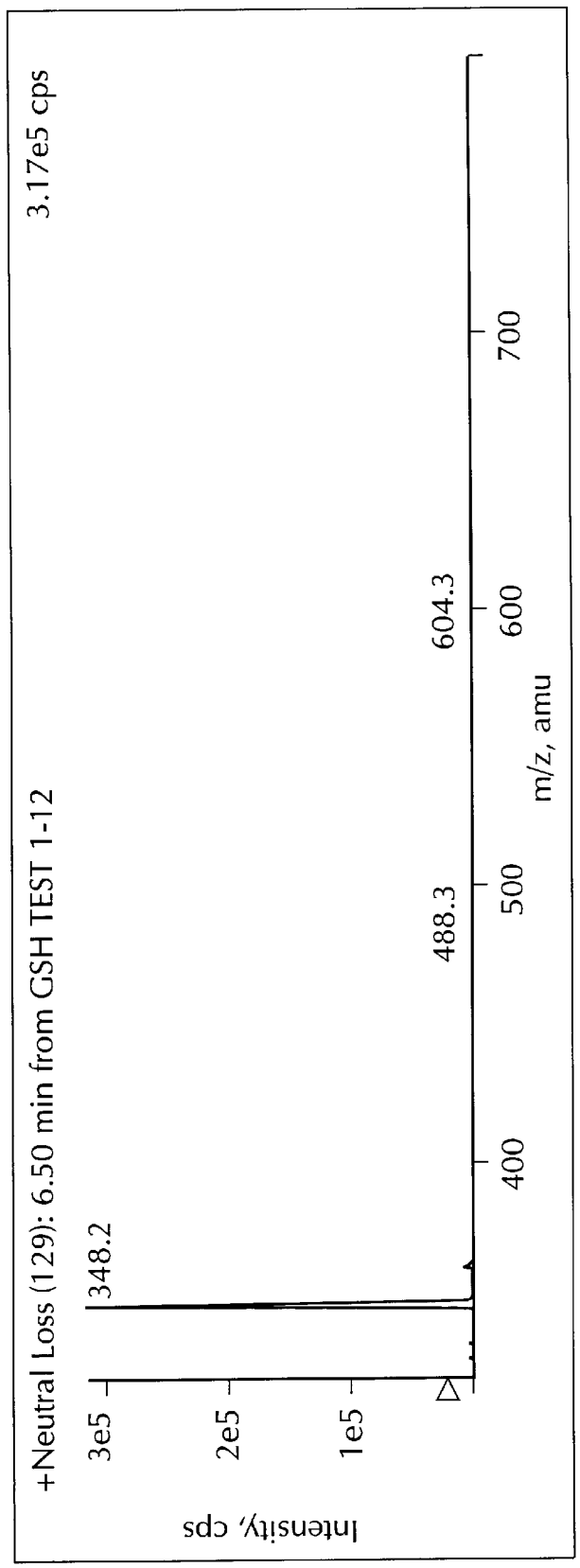

Hess, D. A., Rieder, M. J. (1997) The role of reactive drug metabolites in immune–mediated adverse drug reactions. *Ann Pharmacother.* 31, 1378–1387.

Chasseaud, L. F. (1977) In Arias, I. M., Jakoby, W. B. (eds), Glutathione: *Metabolism and Function*, p. 77, New York, Raven Press.

Baillie, T. A., & Davis, M. R. (1993) Mass spectrometry in the analysis of glutathione conjugates. *Biol. Mass Spectrom.* 22, 319–325.

Janiszewski, J., Schneider, R. P., Hoffmaster, K., Swyden, M., Wells, D., & Fouda, H. G. (1997) Automated Sample Preparation Using Membrane Microtiter Extraction For Bioanalytical Mass Spectrometry. *Rapid Comm. Mass Spectrom.* 11, 1033–1037.

Dahlin, D. C., Miwa, G. T., Lu, A. Y. H., & Nelson, S. D. (1984) N–acetyl–p–benzoquinone imine: a cytochrome P450–mediated oxidation product of acetaminophen. *Proc. Natl. Acad. Sci. U.S.A.* 81, 1327–1331.

Williams, D. P., Pirmahamed, M., Naisbitt, D. J., Maggs, J. L., & Park, B. K. (1997) Neutorphil cytoxicity of the chemically reactive metabolite(s) of clozapine: possible role in agranulocytosis. *J. Pharmacol. Exp. Ther.* 283, 1375–1382.

Madden, S., Maggs, J. L., & Park B. K. (1996) Bioactivation of carbamazepine in the rat in vivo. Evidence for the formation of reactive arene oxide(s). *Drug Metab. Dispos.* 24(4), 469–79.

Ju, C., & Uetrecht, J. P. (1998) Oxidation of a metabolite of indomethacin (desmethyldeschlorobenzoylindomethacin) to reactive intermediates by activated neutrophils, hypochlorous acid, and the myeloperoxidase system. *Drug Metab. Dispos.* 26(7), 676–680.

Schiller, C. D., Gescher, A., & Jheeta, P. (1991) Mechanism of toxicity of the antimelanoma drug 4–hydroxyanisole in mouse hepatocytes. *Eur. J. Cancer* 27(8), 1017–22.

Thompson, D. C., Perera, K., & London, R. (1995) quinone Methide Formation from Para Isomers of Methyphenol (Cresol), Ethytphenol, and Isopropylphenol: Relationship to Toxicity. *Chem. Res. Toxicol.* 8(1), 55–60.

Tang, W., & Abbot, F. S. (1996) Characterization of thiol–conjugate metabolites of 2–propylpent–4–enoic acid (4–ene VPA), a toxic metabolite of valproic acid, by electrospray tandem mass spectrometry. *J. Mass. Spectrom.* 31(8) 926–936.

Roy, Deodutta, & Snodgrass, W. R. (1990) Covalent binding of phenytoin to protein and modulation of phenytoin metabolism by thiols in A/J mouse liver microsomes. *J. Pharmacol. Exp. Ther.* 252(3), 895–900.

Kassahun, K., Hu, P., Grillo, M. P., Davis, M. R., Jin, L., & Baillie, T. A. (1994) Metabolic activation of unsaturated derivatives of valproic acid. Identification of novel glutathione adducts formed through coenzyme A–dependent and independent processes. *Chem.–Biol. Interact.* 90(3), 253–75.

Mays, D. C., Pawluck, L. J., Apseloff, G., Davis, W. B., She, Z. W., Sagone, A. L., & Gerber, N. (1995) Metabolism of phenytoin and covalent binding of reactive intermediates in activated human neutrophils. *Biochem. Pharmacol.* 50(3), 367–80.

Eyanagi, R., Hisanari, Y. & Shigematsu, H. (1991) Studies of paracetamol/phenacetin toxicity: Isolation & characterization of p–amiophenol–glutathione conjugate. *Xenociotica* 21(6) 793–804.

Jin, L., Davis, M. R., Kharasch, E. D., Doss, G. A. & Baillie, T. A. (1996) Identification in Rat Bile of Glutathione Conjugates of Fluoromethyl 2,2–Difluoro–1–(trifluoromethyl)vinyl Ether, a Nephrotoxic Degradate of the Anesthetic Agent Sevoflurane. *Chem. Res. Toxicol.* (9) 555–561.

Wei. T., Stearns, R.A., Stelvio, M. B., Yong, Z, Conrad, R., Braun, M.P., Dean, D.C., Jianmei, P., Kwan, H.L., Doss, G. A., Strauss, J. R., Kwei, G.Y., Rushmore, T.H., Shuet–Hing L.C., Baillie, T.A. (1999) Studies of Cytochrome P–450–Mediated Bioactivation of Diclofenac in Rats & in Human Hepatocytes: Identification of Glutathione Conjugated Metabolites. *Drug Metabolism and Disposition. Amer. Soc. Pharmacology & Expermental Therapeutics.* vol. 27(3):365–372.

Stevens, G. J., Hitchcock, K., Wang, Y.K., Coppola, G.M., Versace, R.W., Chin, J.A., Shapiro, M., Suwanrumpha, S. & Mangold, B.L.K. (1997) In Vitro Metabolism of N–(5–Chloro–2–methylphenyl)–n–(2–methylpropyl) thiourea: Species Comparison and Identification of a Novel Thiocarbamide Glutathione Adduct. *Chem. Res. Toxicol.* vol. 10, 733–741.

Maynard, M.S., Brumback, D. Itterly, W., Capps, T., & Rose, R. (1999) Metabolism of [$^{14}$C] Prometryn in Rats, *J. Agric. Food Chem.*, vol. 47, 3858–3865.

Kassahum, K., Pearson, P.G., Tang, W., McIntosh, I., Leung, K., Elmore, C., Dean, D., Wang, R., Doss, G., & Baillie, T.A., (2001) *Chem. Res. Toxicol.* vol. 14, 62–70.

Baillie, T.A., & Davis, M.R., (1993) Mass Spectrometry in the Analysis of Glutathione Conjugates. *Biological Mass Spectrometry*, vol. 22, 319–325.

* cited by examiner

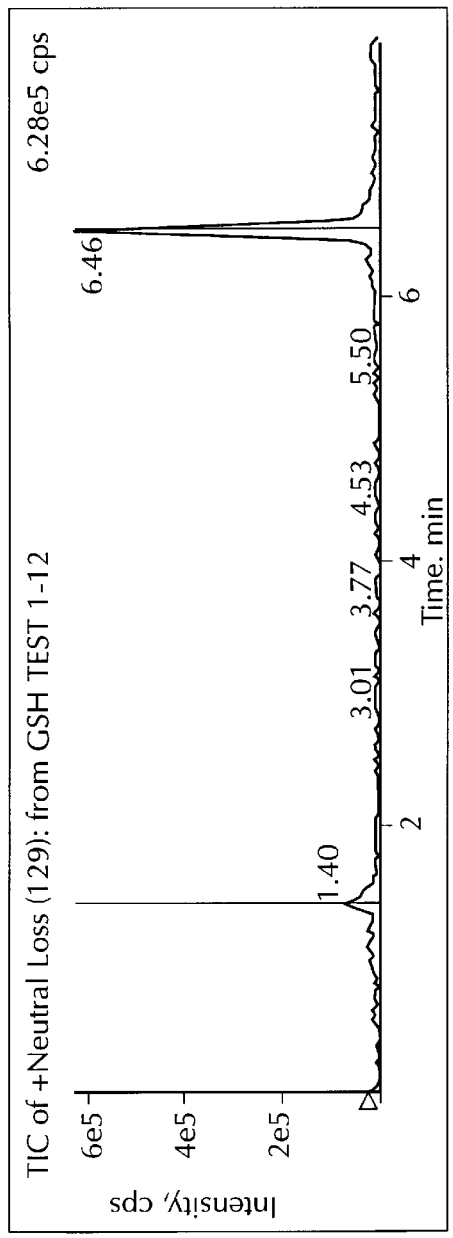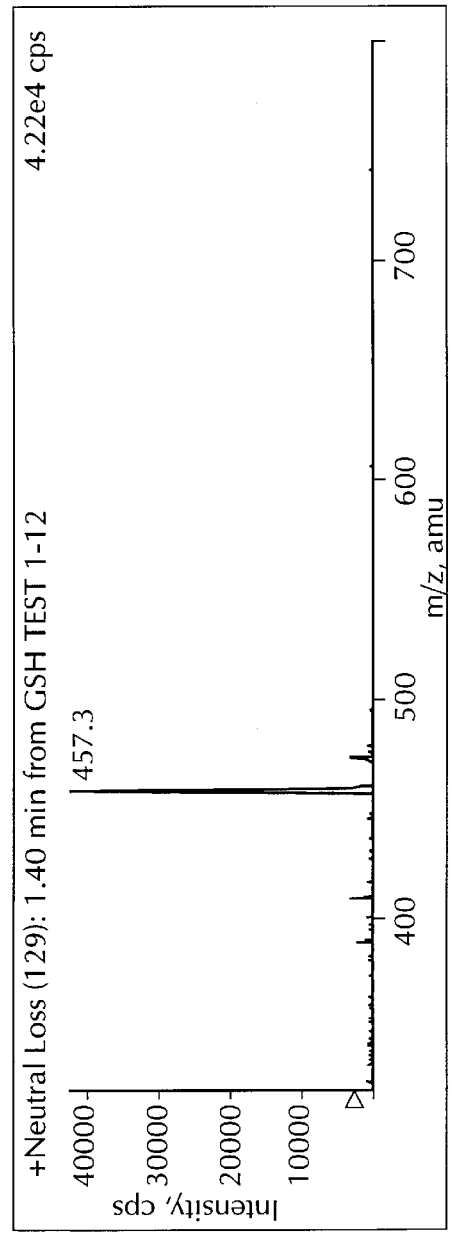

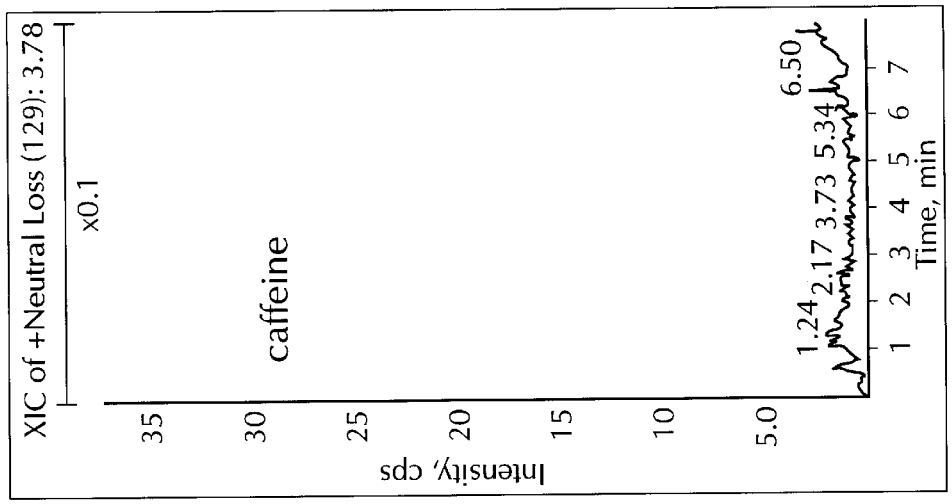
FIG. 2B-1
FIG. 2A-5
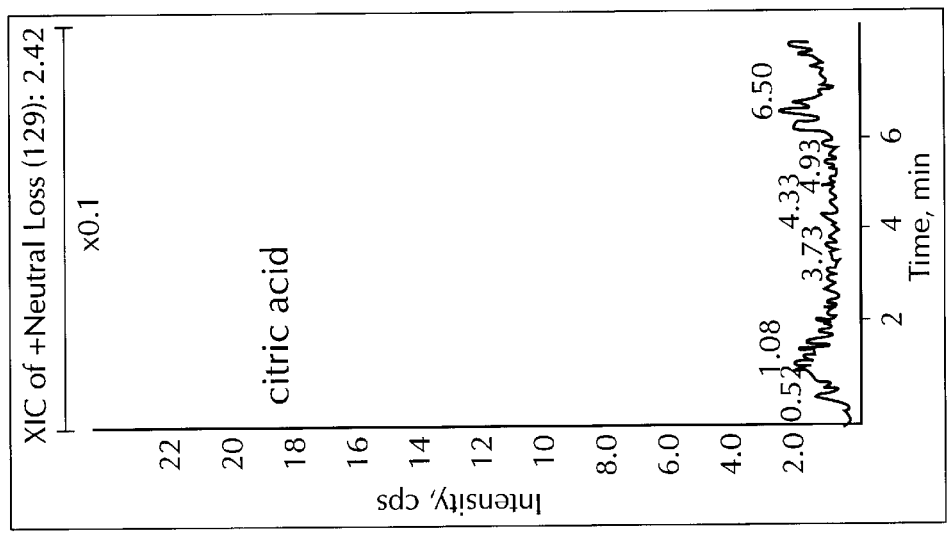
FIG. 2A-4
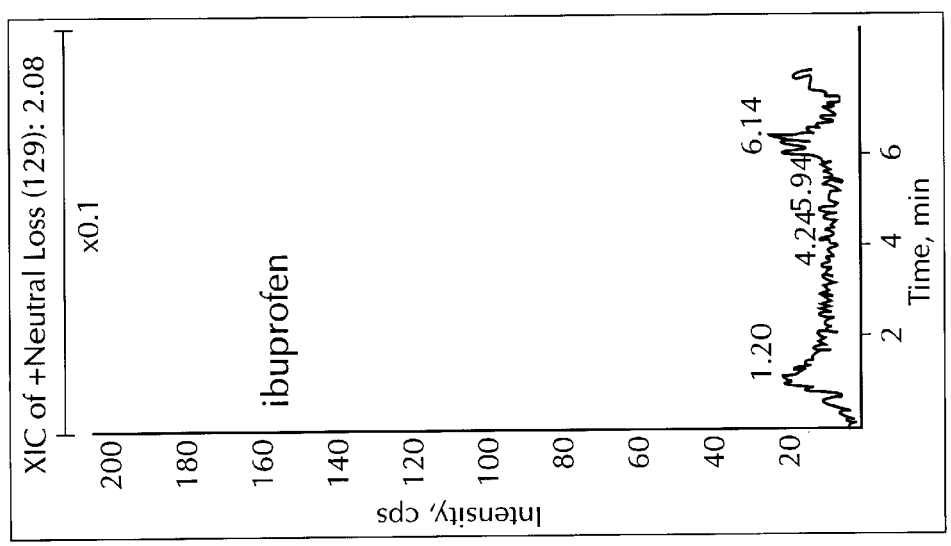

HIGH THROUGHPUT SCREEN FOR REDUCING DRUG CANDIDATE ATTRITION

This application claims benefit of U.S. Pat. No. 60/199,698, filed Apr. 26, 2000.

BACKGROUND OF THE INVENTION

Toxicity of drug candidates accounts for a significant portion of attrition during exploratory development. Following development and commercialization, therapeutic agents exhibiting adverse reactions are less competitive and may ultimately fail in the market place. Implementing a Discovery screen to weed out compounds with potential toxicity early would enable all Discovery candidates entering development to achieve a higher survival rate. Following development, the selected drugs would be more likely to enjoy a competitive advantage and a more favorable therapeutic index.

One common mode of toxicity is the formation of electrophilic reactive metabolites, which manifest their toxicity by covalent binding to nucleophilic groups present in vital cellular proteins and nucleic acids (1–2). Although not all toxicological manifestations are attributable to reactive metabolites, a significant body of literature suggests that inadequate detoxification of chemically reactive metabolites formed as a result of drug bioactivation is a pathogenic mechanism for tissue necrosis (3–4), carcinogenicity (5), teratogenicity (6) and immune mediated toxicity (7).

REFERENCES

1. Nelson, S. D. (1982) Metabolic activation and drug toxicity. *J. Med. Chem.* 25, 753–65.
2. Jollow, D. J., Kocsis, J., Snyder, R., Vainio H. (1977): *Biological Reactive Intermediates.* New York, Plenum Press.
3. Pirmohamed, M., Madden, S. and Park, B. K. (1996) Idiosyncratic drug reactions. *Clin. Pharmacokinet* 31, 215–230.
4. Prescott, L. F. (1983) Reactive metabolites as a cause of hepatotoxicity. *Int. J. Clin. Pharm.* 3, 437–441.
5. Guengerich, F. P. (1992) Metabolic activation of carcinogens. *Pharmacol. Ther.* 54, 17–61.
6. Juchau, M. R., Lee, Q. P., Fantel, A. G. (1992) Xenobiotic biotransformation/bioactivation in organogenesis-stage conceptal issues: implications for embryotoxicity and teratogenesis. *Drug Metab. Rev.* 24, 195–238.
7. Hess, D. A. and Rieder, M. J. (1997) The role of reactive drug metabolites in immune-mediated adverse drug reactions. *Ann Pharmacother.* 31, 1378–1387.
8. Chasseaud, L. F. (1977): In Arias, I. M., Jakoby, W. B. (eds), Glutathione: Metabolism and Function, p. 77. New York, Raven Press.
9. Baillie, T. A., Davis, M. R. (1993) Mass spectrometry in the analysis of glutathione conjugates. *Biol. Mass Spectrom.* 22, 319–325.
10. Janiszewski, J, Schneider, R. P., Hoffmaster, K., Swyden, M., Wells, D., Fouda, H. G. (1997) Automated Sample Preparation Using Membrane Microtiter Extraction For Bioanalytical Mass Spectrometry. *Rapid Comm. Mass Spectrom.* 11, 9.
11. Dahlin, D. C., Miwa, G. T., Lu, A. Y. H. and Nelson, S. D. (1984) N-acetyl-p-benzoquinone imine: a cytochrome P450-mediated oxidation product of acetaminophen. *Proc. Natl. Acad. Sci. U. S. A.* 81, 1327–1331.
12. Williams, D. P., Pirmahamed, M., Naisbift, D. J., Maggs, J. L. and Park, B. K. (1997) Neutrophil cytoxicity of the chemically reactive metabolite(s) of clozapine: possible role in agranulocytosis. *J. Pharmacol. Exp. Ther.* 283, 1375–1382.
13. Madden, Stephen; Maggs, James L.; Park, B. Kevin. (1996) Bioactivation of carbamazepine in the rat in vivo. Evidence for the formation of reactive arene oxide(s). *Drug Metab. Dispos.* 24(4), 469–79.
14. Ju, C,; Uetrecht, J. P. (1998) Oxidation of a metabolite of indomethacin (desmethyldeschlorobenzoylindomethacin) to reactive intermediates by activated neutrophils, hypochlorous acid, and the myeloperoxidase system. *Drug Metab. Dispos.* 26(7), 676–680.
15. Schiller, Claus Dieter; Gescher, Andreas; Jheeta, Parmjit. (1991) Mechanism of toxicity of the antimelanoma drug 4-hydroxyanisole in mouse hepatocytes. *Eur. J. Cancer* 27(8), 1017–22.
16. Thompson, David C.; Perera, Kumar; London, Robert. (1995) Quinone Methide Formation from Para Isomers of Methylphenol (Cresol), Ethylphenol, and Isopropylphenol: Relationship to Toxicity. *Chem. Res. Toxicol.* 8(1), 55–60.
17. Tang, Wei; Abbot, Frank S. (1996) Characterization of thiol-conjugate metabolites of 2-propylpent-4-enoic acid (4-ene VPA), a toxic metabolite of valproic acid, by electrospray tandem mass spectrometry. *J. Mass Spectrom.* 31(8), 926–936.
18. Roy, Deodutta; Snodgrass, Wayne R. (1990) Covalent binding of phenytoin to protein and modulation of phenytoin metabolism by thiols in A/J mouse liver microsomes. *J. Pharmacol Exp. Ther.* 252(3), 895–900.
19. Kassahun, Kelem; Hu, Pei; Grillo, Mark P.; Davis, Margaret R.; Jin, Lixia; Baillie, Thomas A. (1994) Metabolic activation of unsaturated derivatives of valproic acid. Identification of novel glutathione adducts formed through coenzyme A-dependent and independent processes. *Chem.-Biol. Interact* 90(3), 253–75.
20. Mays, Dennis C.; Pawluck, Lew J.; Apseloff, Glen; Davis, W. Bruce; She, Zhi-Wu; Sagone, Arthur L.; Gerber, Nicholas. (1995) Metabolism of phenytoin and covalent binding of reactive intermediates in activated human neutrophils. *Biochem. Pharmacol.* 50(3), 367–80.

SUMMARY OF THE INVENTION

This invention provides a method for identifying drug candidates which produce reactive metabolites which comprises:

(a) incubating said drug candidates with a microsomal drug metabolizing enzyme system in the presence of glutathione and;

(b) detecting glutathione conjugates formed in step (a).

This invention further provides a method for identifying drug candidates which produce reactive metabolites which is a high throughput method.

This invention further provides a method for identifying drug candidates which produce reactive metabolites wherein said drug metabolizing enzyme system is a human liver system.

This invention also provides a method for identifying drug candidates which produce reactive metabolites which comprises: incubating said drug candidates with a microsomal drug metabolizing enzyme system in the presence of glutathione and detecting glutathione conjugates by tandem mass spectometry.

DETAILED DESCRIPTION OF THE INVENTION

This invention provides a high throughput method of identifying candidates with the potential to produce reactive metabolites. It exploits one of the natural mechanisms for eliminating reactive intermediates: conjugation with glutathione. Through its nucleophilic sulfhydryl group, glutathione protects vital cellular constituents against chemically reactive species which bind to the reactive electrophilic moiety, to form stable S-substituted adducts (8). The detoxification of the acetaminophen electrophilic metabolite by glutathione is one of the classic examples of that protection.

A universal analytical method for detecting glutathione conjugates, which are generated by in vitro incubation with human liver microsomal drug metabolizing enzyme systems and with glutathione, will identify compounds that undergo bioactiviation to reactive metabolites. This analytical method utilizes tandem mass spectrometry. During collision induced dissociation, all glutathione adducts undergo the neutral loss of the pyroglutamic acid moiety (129 Da). The diagnostic neutral loss of 129 Da allows the specific detection of any glutathione conjugates that have been generated via metabolic activation followed by conjugation (9).

The method of this invention is reliable, rapid, simple and amenable to high throughput automation. The incubation step can easily be automated following the heated block 96 well incubation method developed by J. Janiszewski. The sample preparation and extraction step is automated using Quadra 96 SPE (10). The analytical step is particularly simple requiring no compound specific optimization. Although we have utilized chromatography with 7-minute runtime, the specificity of the assay suggests that a runtime of 1 minute per sample is feasible. Consequently, throughput of more than 1000 compounds a day can be attained by utilizing the dual column switching system.

The method will detect most toxic compounds whose toxicity is mediated by reactive metabolites generated by bioactivation with drug metabolizing oxidative P450 systems. It will not detect reactive metabolites that do not form stable adducts with glutathione (such as free radicals) or those formed by non-microsomal enzymes.

EXAMPLES

In vitro Incubation and Sample Preparation

Human liver microsomal (HL-mix-11) incubation mixture containing 500 µM substrate, 1 mM glutathione (GSH), 1 µM P450 and 100 mM potassium phosphate buffer (pH 7.4) was pre-incubated for 3 minutes at 37° C. The reaction was initiated by the addition of an NADPH-generating system (0.54 mM NADP$^+$, 10 mM MgCl$_2$, 6.2 mM DL-isocitric acid and 0.5 U/ml isocitric dehydrogenase). The final incubation volume was 1 mL. Samples without NADPH or substrates are used as negative controls. After 30 minutes incubation at 37° C., the incubation mixture was centrifuged at 3,500 rpm for 10 minutes. The supernatant was prepared by automated 96-well solid phase extraction (10). This included removing proteins, washing 3 times with 100 µl of water and eluting with 100 µl of acetonitrile. Following solvent evaporation, the residues were dissolved in 100 µl of starting mobile phase.

HPLC/MS Analysis

Chromatographic separations utilized an HP 1100 quaternary HPLC pump after injection by a CTC PAL autosampler. Aliquots (20 µl) of prepared samples were injected onto a 2×30 C18 column packed with 3 µm particles. The analyses were performed using a mobile phase flow rate of 0.2 ml/min and a fast gradient of from 5/95 acetonitrile/10 mM ammonium acetate to 80/20 over a 5 minute period after an initial hold of 1 minute. The HPLC column eluant was introduced into the Turbolonspray source of a SCIEX API 3000 triple quadrupole mass spectrometer. The ion source utilized 6 L/sec nitrogen drying gas and was operated in the positive ion mode at 5200V, 450° C. and a nebulizer setting of 7. Nitrogen was used as a curtain gas, at a setting of 9, and, as collision gas, at a setting of 5. Positive ions formed in the ion source were sampled into the vacuum chamber through an orifice held at 10V and collisionally activated in the second quadrupole at laboratory frame energy of 19.4 eV. The mass spectrometer was operated in the neutral loss mode, scanning over a range of m/z 320 to 800 in about 2.4 seconds.

Application to Selected Drugs with Known Toxicity Profiles

The current method was validated by application to 20 commercially available therapeutic agents representing diverse chemical structures and toxicity profiles. Half of the compounds (Table 1) are known to posses desirable safety profiles. The other half (Table 2) are known to produce reactive metabolites.

Figures 2, 2A, 3:
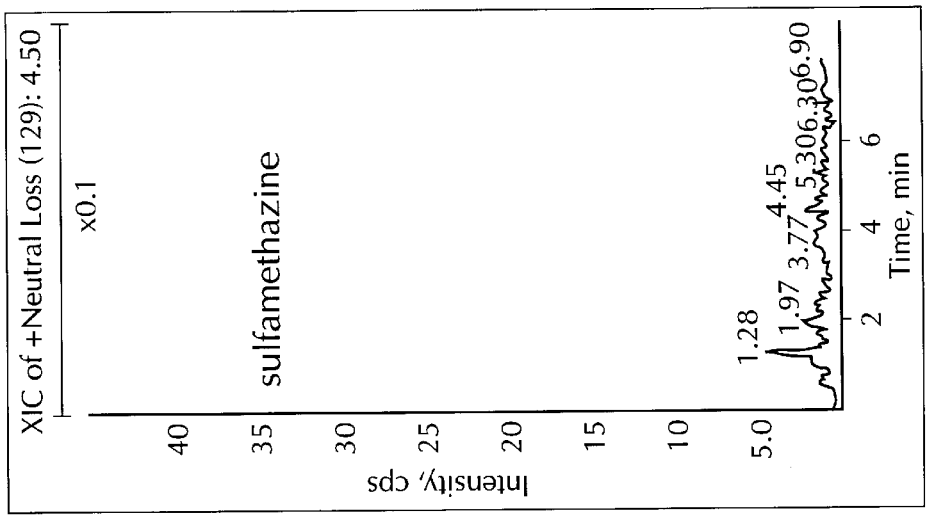
Figures 2, 2A:
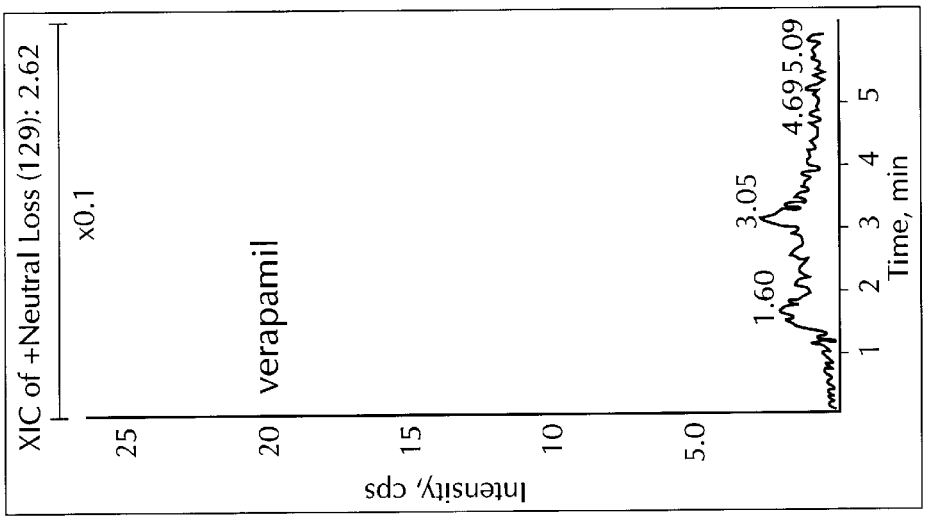
Figures 1, 2A:
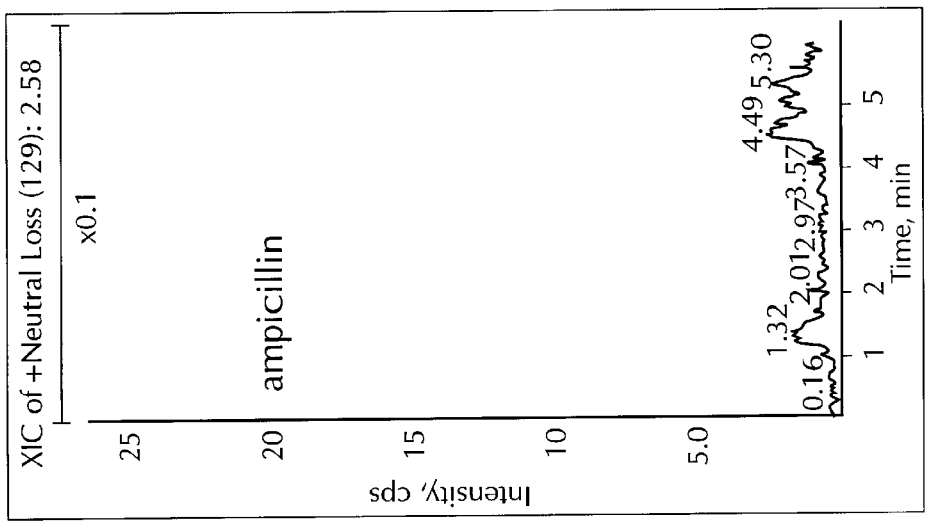

Control samples without NADPH or substrate showed the appearance of a late eluting matrix peak representing a response at m/z 348 (FIG. 1). Since the mass to charge ratio of a GSH molecule ion is 308, this matrix peak can be eliminated by starting the scan range slightly higher (350 instead 320 m/z). The chromatograms shown in FIGS. 2–4 were obtained by reconstructing the ion current from m/z 350 to 800. It is recommended that for every set of samples negative and positive control samples be included.

Results from the validation with 20 commercially available compounds (FIGS. 2–4) demonstrated that the current method reliably detects the formation of reactive metabolites. Each of the 10 compounds that possess desirable safety profile produced negative responses (FIG. 2). This suggests that the method is not likely to produce false positive responses.

Eight out of the 10 compounds that are known to generate reactive metabolites produced positive responses (FIG. 3). These positive responses cover a broad range of reactive metabolites (Table 1), including quinone imine (acetominophen and indomethacin), nitrenium (clozapine), epoxide (carbamazepine), quinone (4-hydroxyanisole) and quinone methide (m-cresol, p-cresol and 4-isopropylphenol). The formation of the reactive metabolite from indomethacin requires several sequential oxidation steps (13). These results suggest that the current method detects most reactive metabolites including those resulting from multiple oxidation steps.

Figures 2, 2B, 3, 4:
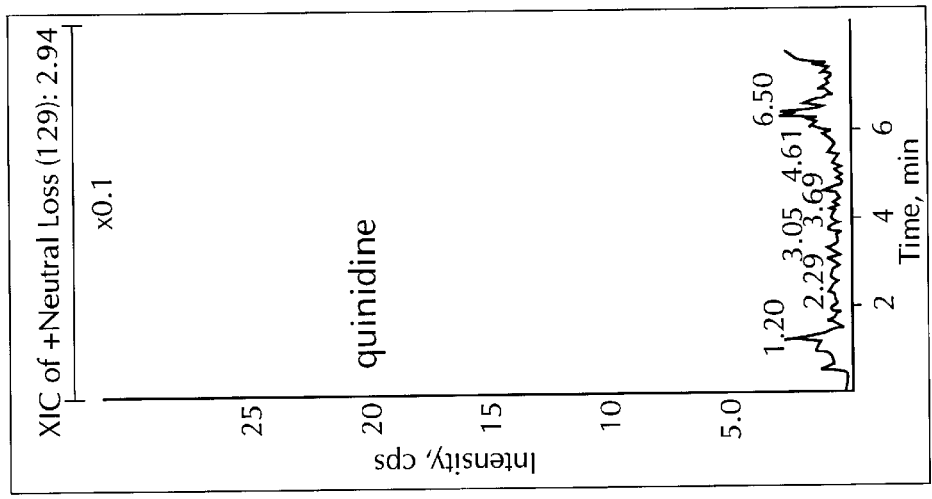
Figures 2, 2B, 3:
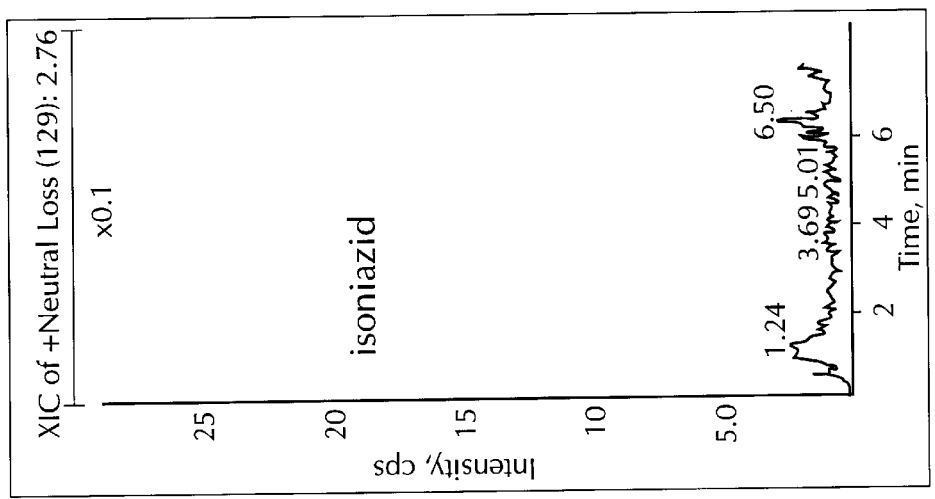
Figures 2, 2B:
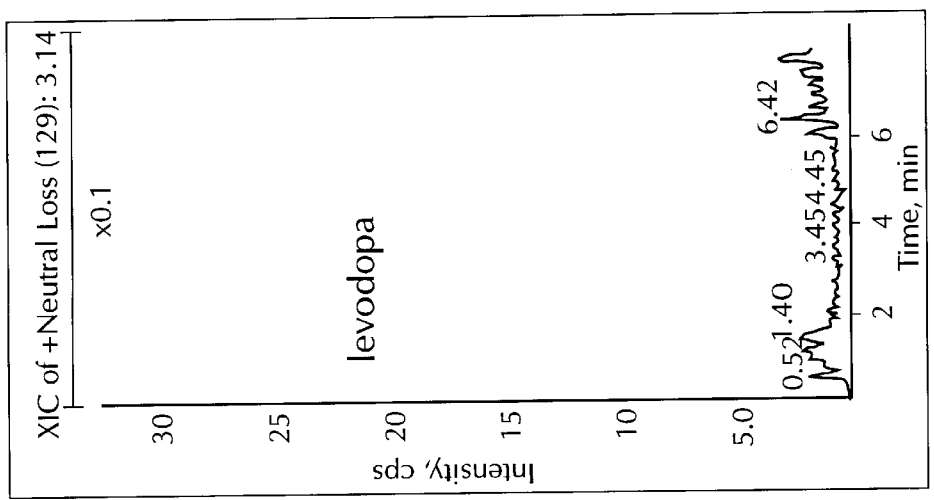
Figures 2, 2B, 3, 4, 5:
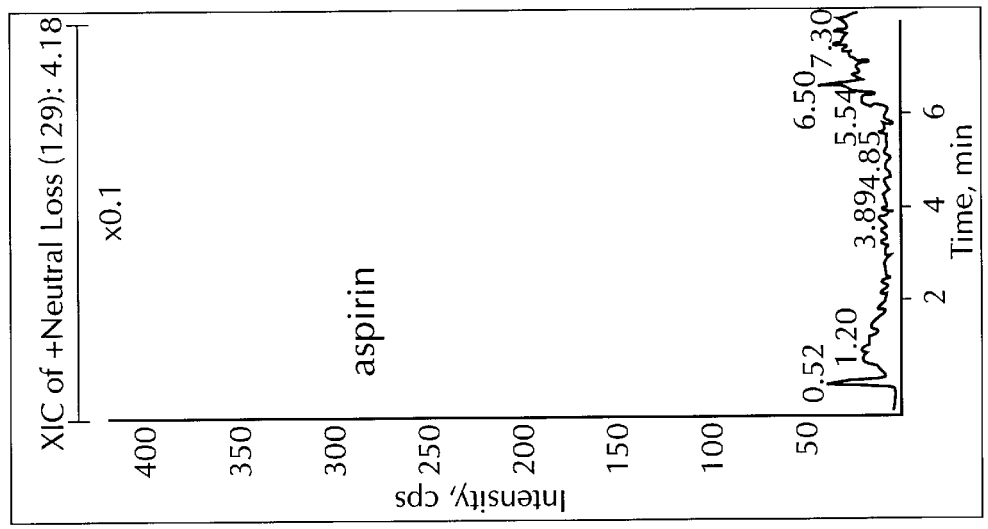
Figure 3B:
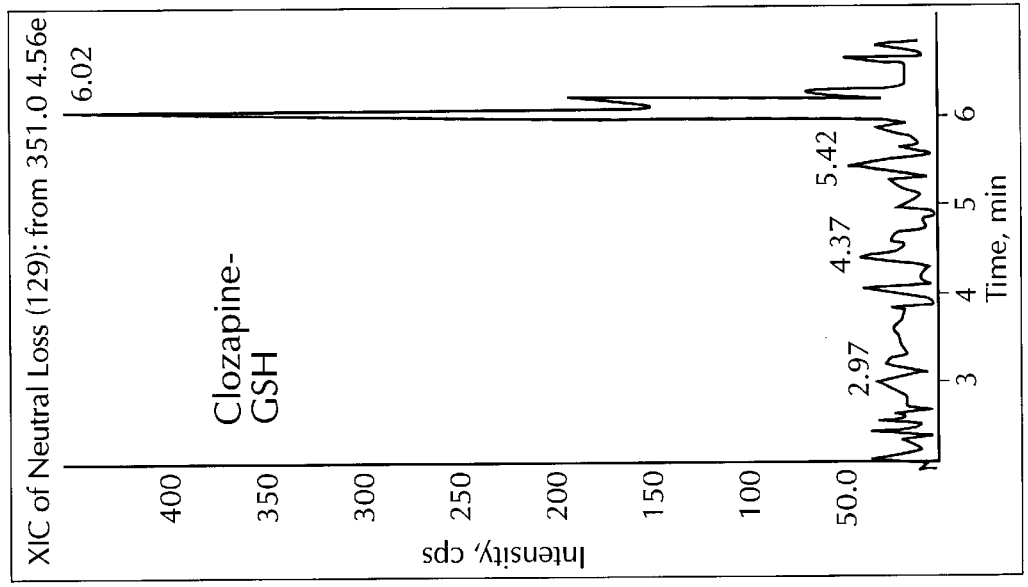
Figure 3A:
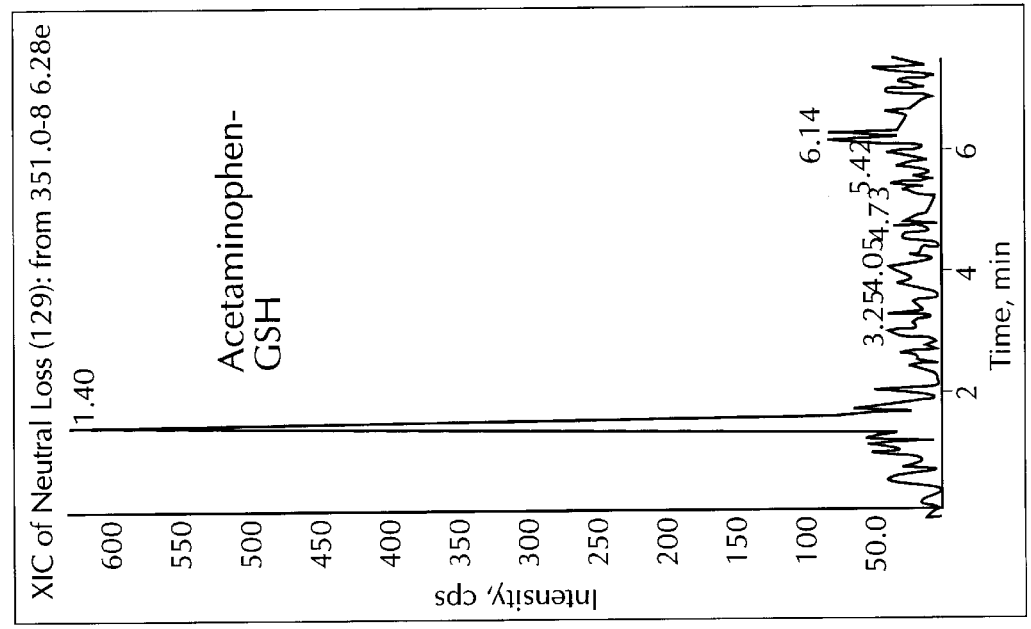
Figure 3D:
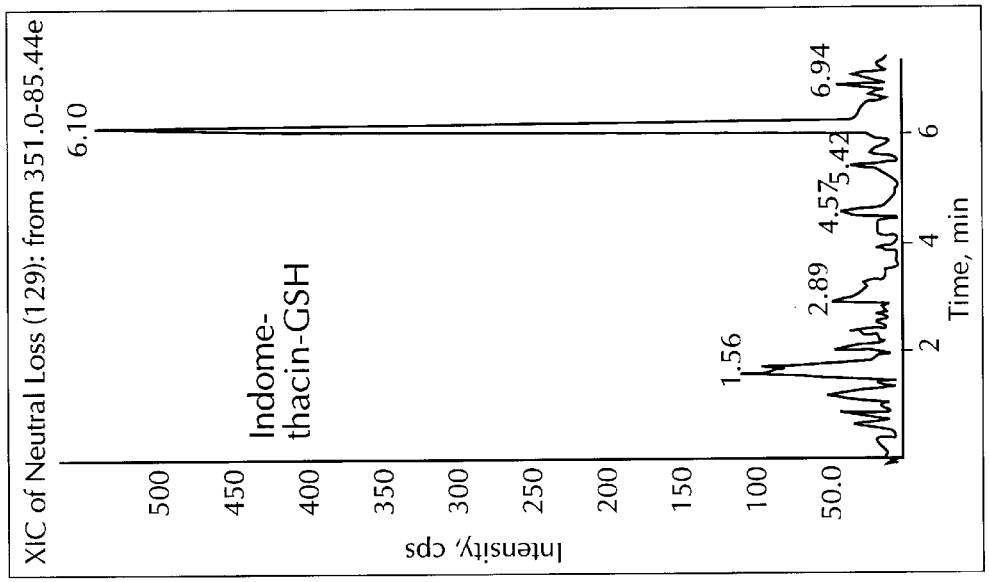
Figure 3C:
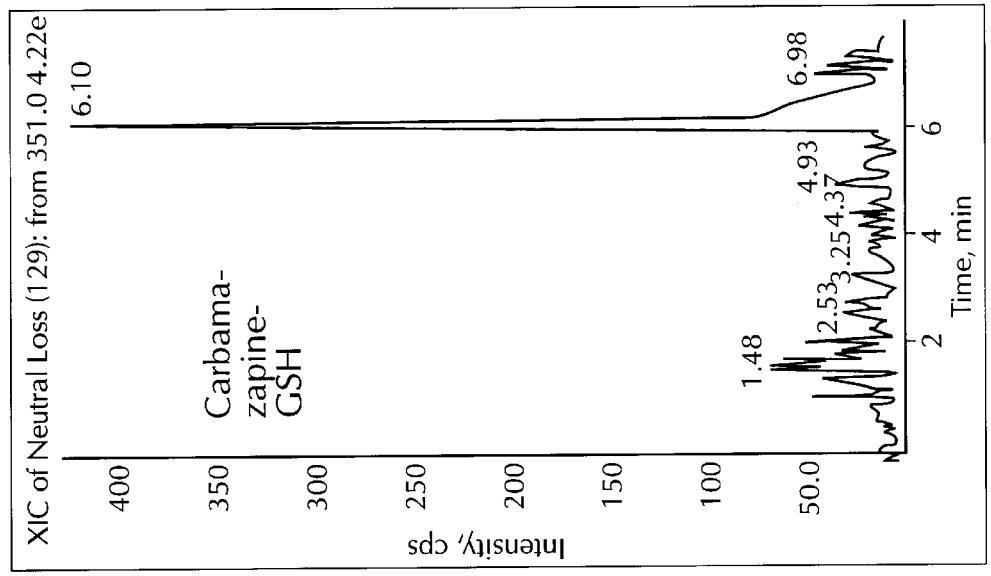
Figure 3F:
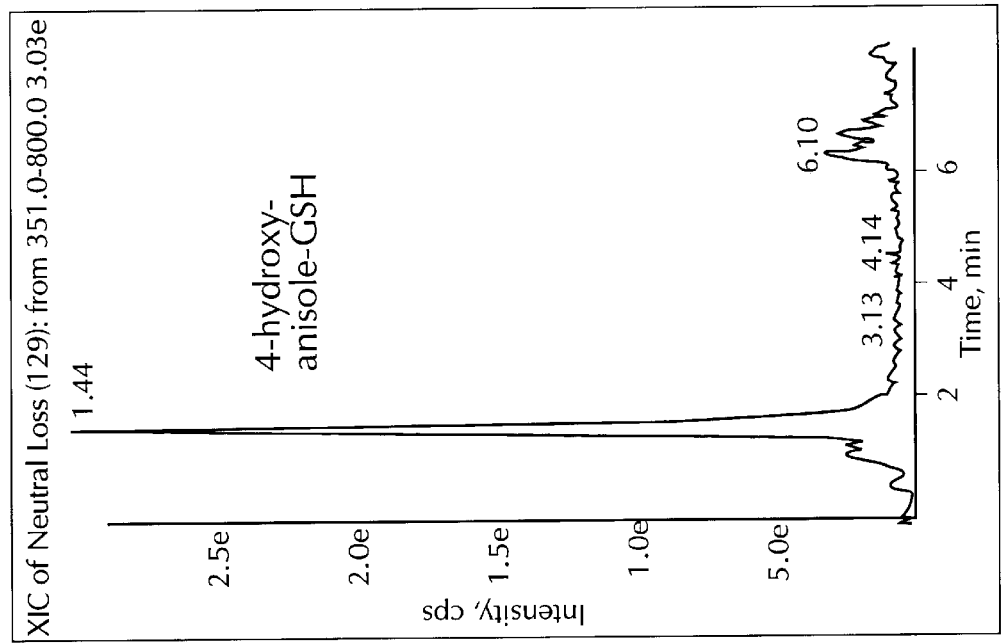
Figure 3E:
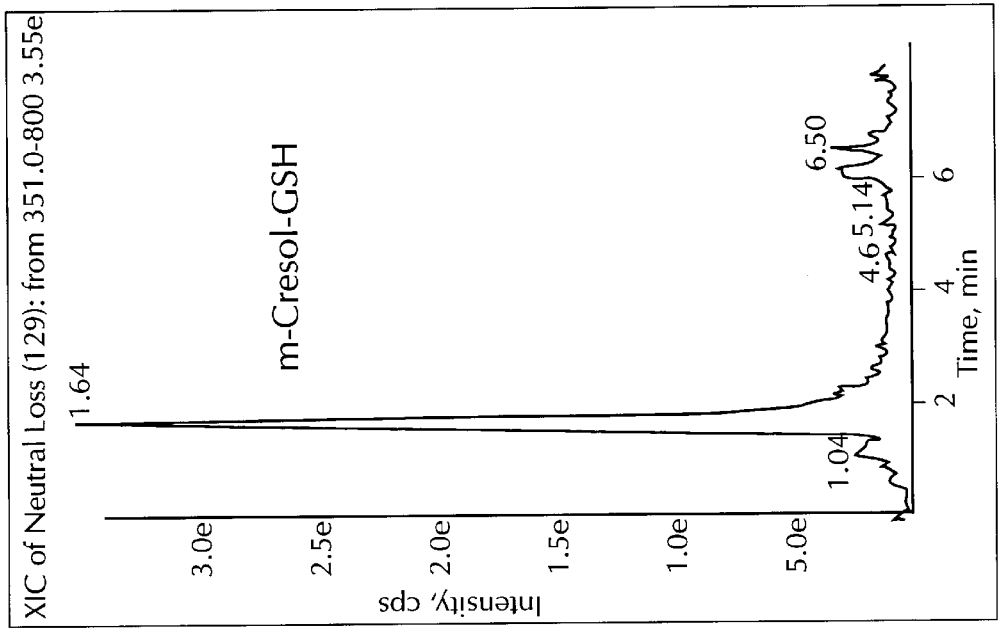
Figure 3H:
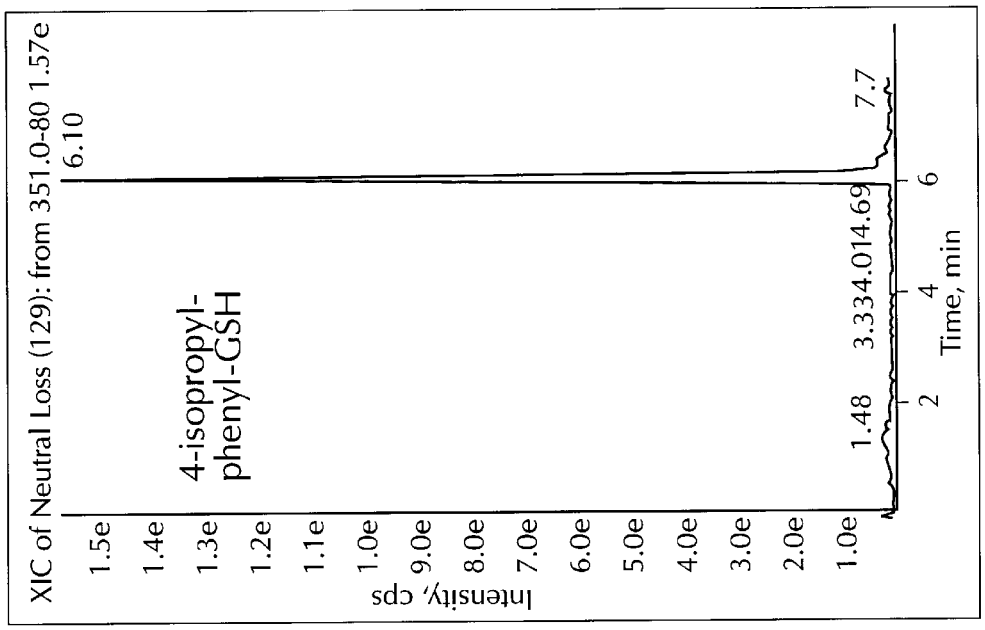
Figure 3G:
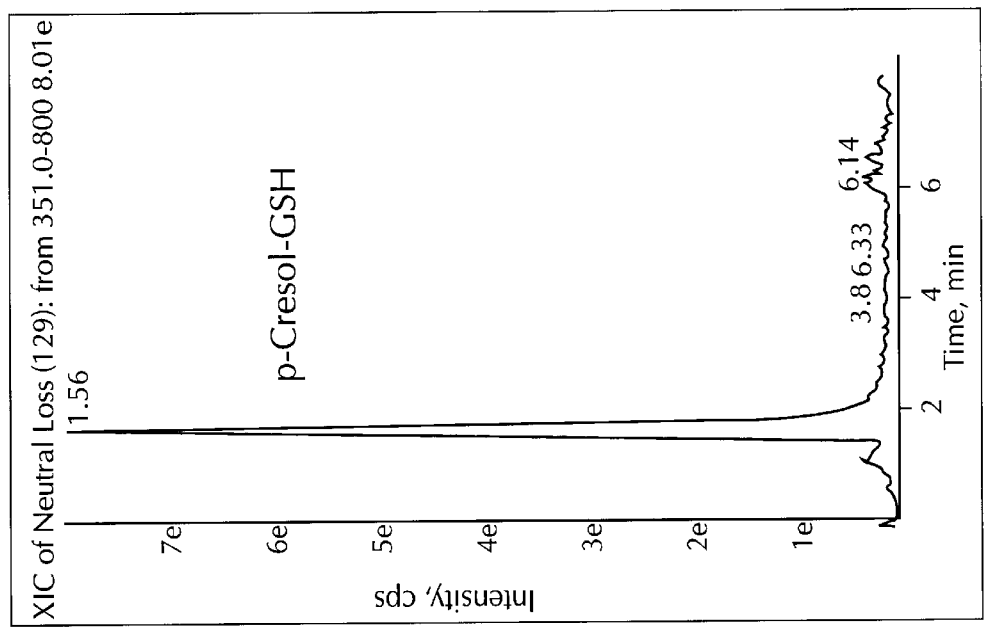
Figure 4A:
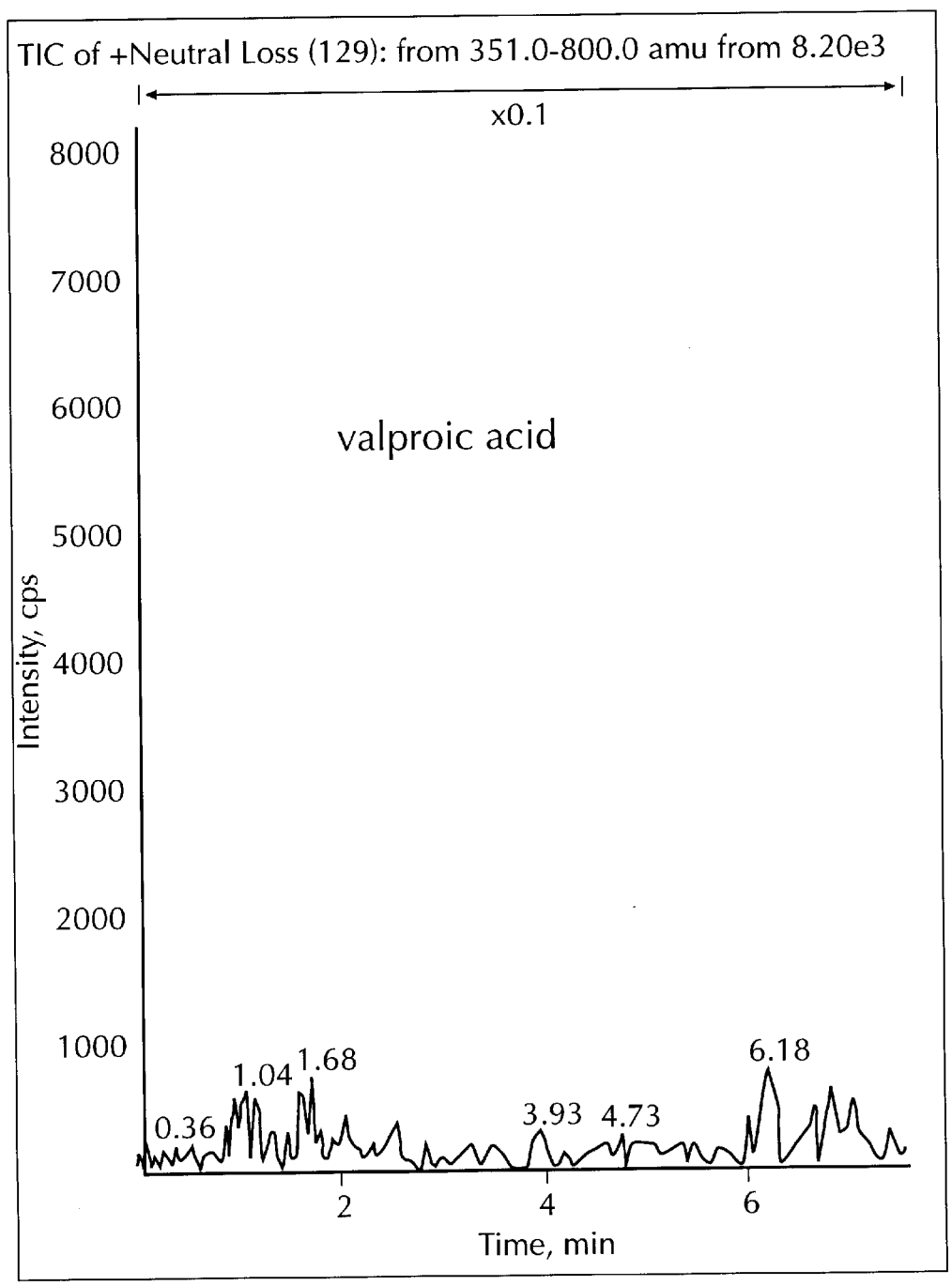
Figure 4B:
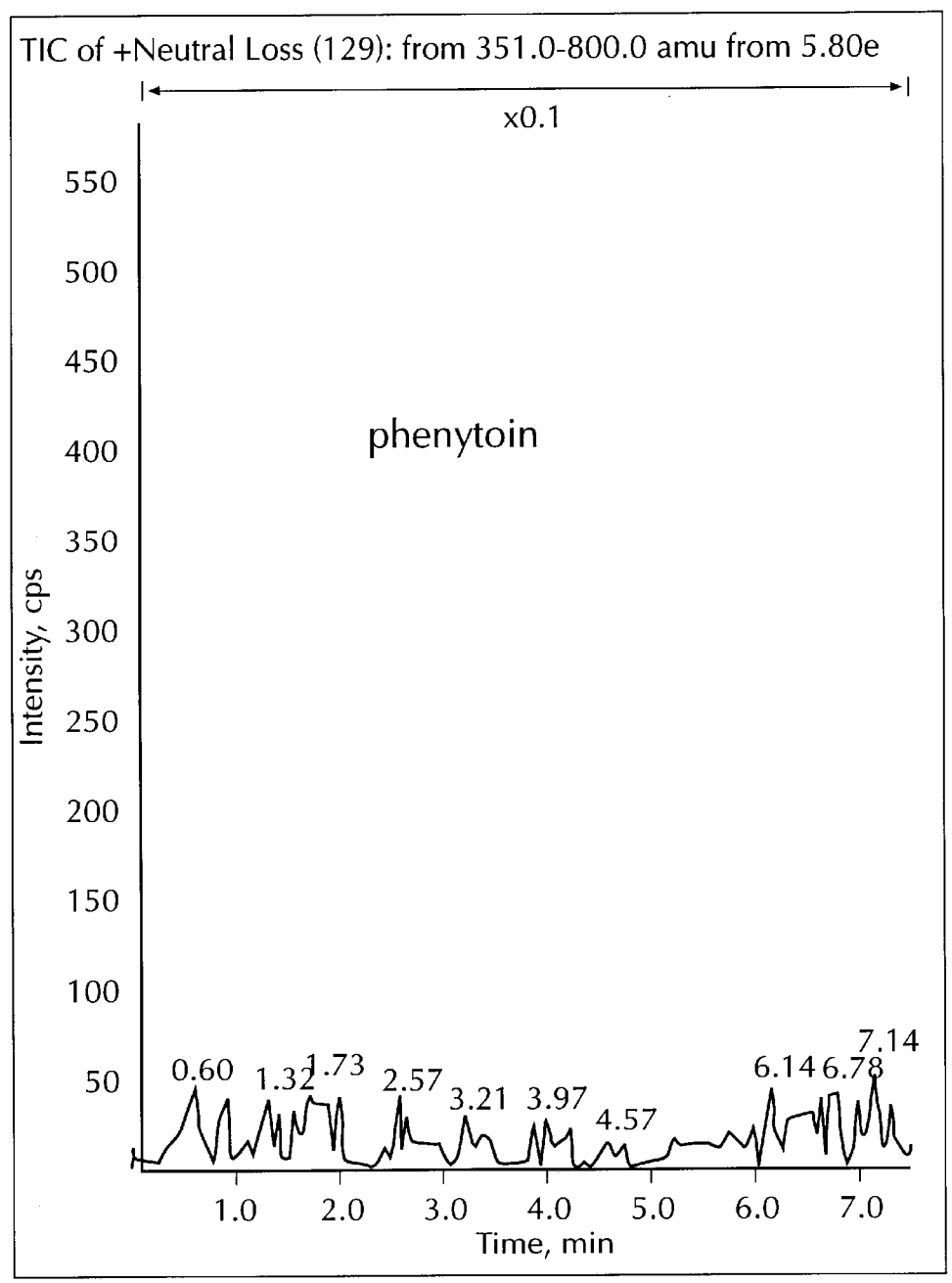

The two compounds that are known to generate reactive metabolites but did not produce positive responses in the current assay are valproic acid and phenytoin (FIG. 4). However, it is well documented that the formation of the valproic acid reactive metabolite (2,4-diene-VPA) requires not only microsomal P450-oxidation to form 4Oene VPA but also β-oxidation catalyzed by a mitochondrial Coenzyme A dependent process to form 2,4-diene-VPA (19). For phenytoin, the reactive metabolite is a free radical instead of an epoxide (20). GSH can reduce the free radical and reduce covalent binding of phenytoin, but GSH can not form a stable adduct with it. Clearly the current screen detects only those reactive metabolites formed by bioactivation via microsomal P450 systems and specifically those forming stable adducts with glutathione.

Three of the compounds tested produce quinone methide reactive metabolites. The peak responses of the neutral loss scan of 129 correlated very well to the previously documented (6) relative quinone methide formation rates, i.e., m-cresol<p-cresol<4-isoproylphenol (FIG. 2). This suggests that the proposed screen can potentially be used to compare the extent of reactive metabolite formation for several compounds in the same series.

TABLE 1

List of commercially available drugs that are not known to form reactive metabolites.

| Name (Therapeutic uses) | Structure |
|---|---|
| Ampicillin (Antibiotics) | 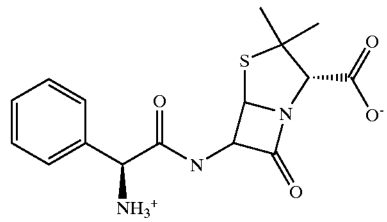 |
| Verapamil (Cardiovascular agent) | 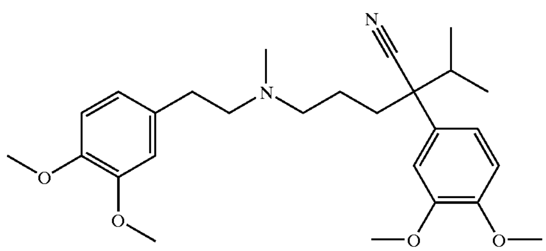 |
| Sulfamethazine (Antibacterials) | 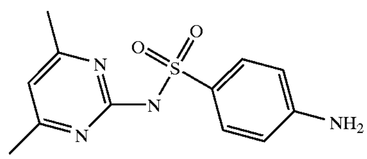 |
| Ibuprofen (Anti-inflammatory analgesics) | 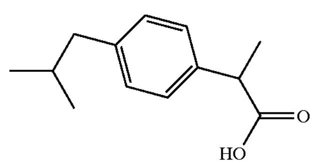 |
| Citric acid (Acidulant) | 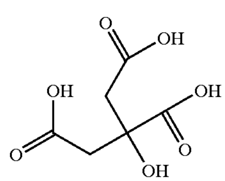 |
| Caffeine (Analeptics) | 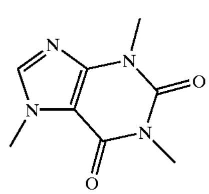 |
| Levodopa (Parkinson's disease) | 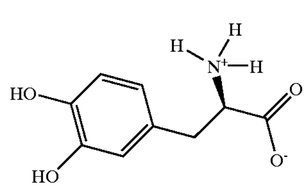 |

TABLE 1-continued

List of commercially available drugs that are not known to form reactive metabolites.

| Name (Therapeutic uses) | Structure |
| --- | --- |
| Isoniazid (Antitubercular agent) | 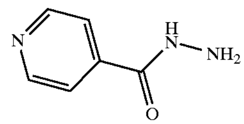 |
| Quinidine (Antiarrhythmic agent) | 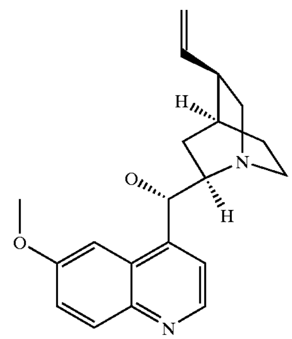 |
| Aspirin (Anti-inflammatory analgesics) | 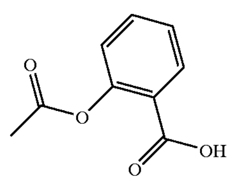 |

TABLE 2

List of commercially available drugs whose toxicities have been linked to formation of reactive metabolites.

| Name (Ther. uses) | Structure | Reactive Metabolite | Toxicity (Ref.) |
| --- | --- | --- | --- |
| Acetaminophen (Anti-inflammatory analgesics | 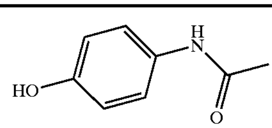 | | Hepato-toxicity (11) |
| Clozapine (Antipsychotic) | | | Neutrophil Cyto-toxicity (12) |

TABLE 2-continued

List of commercially available drugs whose toxicities have been linked to formation of reactive metabolites.

| Name (Ther. uses) | Structure | Reactive Metabolite | Toxicity (Ref.) |
|---|---|---|---|
| Carbamazepine (Anticonvulsant) | 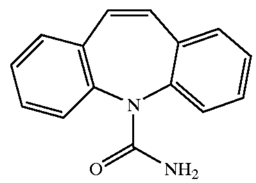 | | Hypersensitivity (13) |
| Indomethacin (Anti-inflammatory analgesics) | 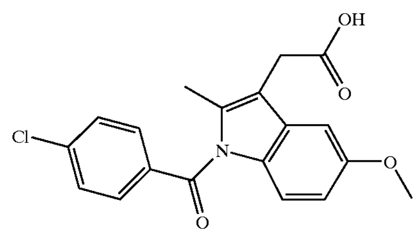 | | Neutrophil toxicity (14) |
| 4-hydroxy-anisole (Antimelanoma) | | | Hepatotoxicity (15) |
| m-Cresol (Local anti-infective agent) | 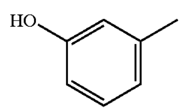 | | Circulatory collapse, death (16) |
| p-cresol (Local anti-infective agent) | 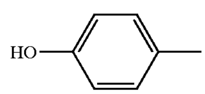 | | Circulatory collapse, death (16) |
| 4-isoproyl-phenol (Analog of p-cresol) | 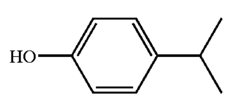 | | Circulatory collapse, death (16) |
| Valproic acid (Anticonvulsant) | 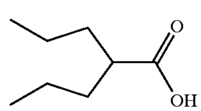 | | Hepatotoxicity (17) |
| Phenytoin/Anticonvulsant | 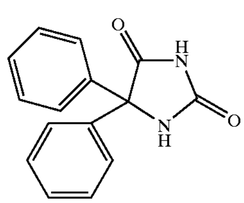 | | Hepatotoxicity (18) |

What is claimed is:

1. A high throughput discovery screen for determining the potential toxicity of candidate drugs comprising the steps of:

(a) incubating the candidate drugs, in a first multi-well plate, with a microsomal enzyme metabolizing system wherein said drugs may form reactive electrophilic metabolites;

(b) permitting said electrophilic metabolites to react with glutathione in order to form glutathione conjugates;

(c) processing the samples, containing glutathione-drug cpnjugates, via an automated solid phase extraction system, in order to prepare a further multi-well plate from which the conjugates can be extracted for automated HPLC;

(d) conducting HPLC column runs on said extracts in order to generate HPLC eluates containing said conjugates;

(e) introducing said eluates, at source, into a triple quadrapole mass spectrometer, and (f) detecting said conjugates with tandem (MS—MS) mass spectrometry.

2. The method of claim 1, wherein said microsomal enzyme metabolizing system is a human liver system containing cytochrome P450 enzymes.

3. The method of claim 1, wherein said automated solid phase extraction system is provided by a Quadra 96 programmable pipetting workstation.

4. The method of claim 1, wherein HPLC is conducted using a CTC PAL autosampler.

5. The method of claim 1, wherein the chromatography run time is 7 minutes.

6. The method of claim 5, wherein the chromatography run time is 1 minute.

7. The method of claim 6, wherein a dual column switching system is employed and throughput of more than 1000 compounds per day is attained.

8. The method of claim 1 wherein detection of glutathione conjugates via tandem mass spectrometry is made by operating the spectrometer in collisional neutral loss mode, with specific detection of the 129 Dalton pyroglutamic acid moiety of a glutathione-drug adduct.

* * * * *